United States Patent [19]
Cumming

[11] Patent Number: 5,984,914
[45] Date of Patent: Nov. 16, 1999

[54] APPARATUS AND METHOD FOR CORNEAL KERATOTOMY

[76] Inventor: J. Stuart Cumming, 1211 W. LaPalma Ave., #201, Anaheim, Calif. 92801

[21] Appl. No.: 09/109,886

[22] Filed: Jul. 3, 1998

[51] Int. Cl.⁶ .................................................. A61B 17/36
[52] U.S. Cl. .................................................. 606/4; 606/17
[58] Field of Search ............................. 606/4–6, 15, 16, 606/10–12, 14–17

[56] References Cited

U.S. PATENT DOCUMENTS

| | | | |
|---|---|---|---|
| 4,820,264 | 4/1989 | Matsui et al. | 606/4 |
| 5,215,104 | 6/1993 | Steinert | 606/4 |
| 5,217,459 | 6/1993 | Kamerling | 606/48 |
| 5,312,394 | 5/1994 | Beckman | 606/6 |
| 5,323,788 | 6/1994 | Silverstrini et al. | 606/5 |
| 5,688,264 | 11/1997 | Ren et al. | 606/4 |
| 5,722,970 | 3/1998 | Colvard et al. | 606/4 |
| 5,722,971 | 3/1998 | Peyman | 606/4 |
| 5,752,967 | 5/1998 | Kritzinger et al. | 606/5 |
| 5,779,696 | 7/1998 | Berry et al. | 606/5 |

*Primary Examiner*—Linda C. M. Dvorak
*Assistant Examiner*—Sonja C. Harris
*Attorney, Agent, or Firm*—Boniard I. Brown

[57] ABSTRACT

Improved laser keratotomy is provided by defining a pocket in a cornea and insertion thereinto of a spatula or cutting blade having thereon reflective or opening means for controlling application of a laser beam to corneal tissue in anterior or posterior pocket walls to control and define areas of ablation of corneal tissue.

42 Claims, 3 Drawing Sheets

APPARATUS AND METHOD FOR CORNEAL KERATOTOMY

BACKGROUND AND SUMMARY OF THE INVENTION

The present invention provides advances in corneal laser keratotomy which greatly reduce the risk of major operative and long term complications.

Heretofore, laser keratotomy procedures have often involved relatively extensive procedures with substantial probability of complications. One such procedure, identified as LASIK (an acronym for Laser In Situ Keratomileusis), involves the cutting of a flap over a wide area of the cornea. Because corneal tissue does not heal, when such flap is replaced in position, only an outside layer of ephithelial cells grows over the interface to provide the only means of holding the flap in position. Such layer of cells is only about 6 or 7 cells thick and is the only support that holds the flap in position. In the event that the patient's eye is impacted, rubbed, etc., such flap may break loose, as occurs relatively frequently, requiring further and often serious procedures.

In accordance with the present invention, a slit is made with a sharp blade into the anterior cornea to a predetermined depth. A pocket is defined by separating corneal lamellae by employing a blunt dissector manipulated by the surgeon to define either a straight pocket, with linear edges, or by utilizing a curved dissector, to define an arcuate pocket or arcuate segments, in accordance with the particular needs of a patient.

The pocket in the cornea may also be defined by an automated keratome having a sharp cutting blade or trephine, vibrating at very high rates.

A spatula or glide is inserted into the pocket thus formed. The spatula has thereon means for defining the configuration of laser ablation of the corneal tissue. Reflective or mirror areas on the spatula reflect the laser beam onto the anterior wall of the pocket. In using a spatula with openings defined therein the laser beam passes through such opening or openings for ablation of the posterior wall of the pocket.

The reflective areas or openings may be defined on or in the dissector or the blade of the keratome which remains in the pocket after the pocket is cut. The dissector or keratome blade remains in the pocket during laser ablation.

After the ablation of corneal tissue, the blade or spatula is removed from the pocket, whereupon the walls of the pocket are urged together by normal pressure in the eye, with resultant change in the configuration of the cornea interior surface.

DESCRIPTION OF THE PREFERRED EMBODIMENTS

Figure 1:
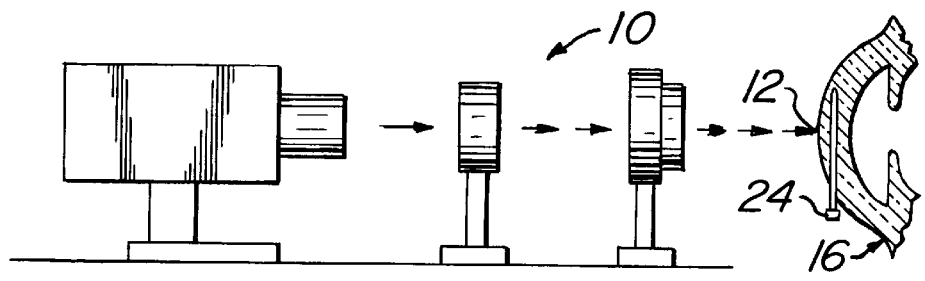
FIG. 1 is a general illustration of laser equipment and a laser beam therefrom, in relation to an eye cornea having therein a pocket and spatula according to the invention.
Figure 2:
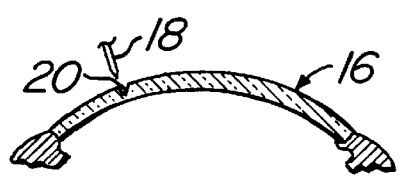
FIG. 2 is a sectional view of the anterior portion of an eye, showing the cutting of a slit in the cornea.

Referring to the drawings, a preferred embodiment of the invention is shown as comprising laser means 10 for generating a laser beam 12 to impinge on a spatula or glide 14 disposed in a pocket defined in the cornea of an eye 16 of a person.

In accordance with the invention, a sharp blade 18 defines a slit or cut 20 in the cornea to a predetermined depth.

A pocket or tunnel 23 is defined in a generally chordal position in the cornea by insertion via the slit 20 of a blunt dissector 22 or by an automated keratome (not shown), to define in the cornea a pocket having linear or curved, arcuate edges, in accordance with requirements of particular patients.

Figure 3:
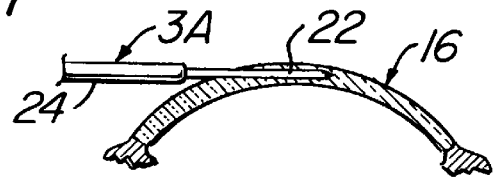
FIGS. 3 and 3A show the anterior portion of an eye with a blunt dissector in a pocket defined in the cornea, and showing a curved dissector for defining a pocket for correction of astigmatism.
Figure 3A:
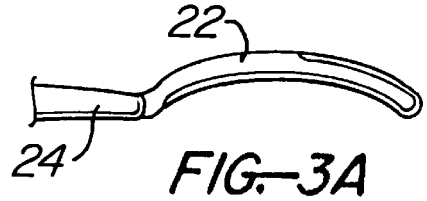
Figure 4:
FIG. 4 is a sectional view of the anterior portion of an eye, and showing a suction ring and a trephine or cutting blade of an automatic keratome in relation thereto.

The blunt dissector, manipulated by the surgeon by handle 24 is manipulated to separate corneal lamellae to define a straight pocket having linear edges or an arcuate pocket having curvilinear edges, depending upon the utilization of either a linear blade (not shown) or an arcuate blade 22 (FIGS. 3 and 3A). The pocket in the cornea may be formed by an automatic keratome, electrical or hydraulic (not shown) which employs a sharp cutting blade or trephine, a thin typically metallic blade vibrating at thousands of vibrations per second. The keratome ultrasonic cutter moves in a smooth, controlled manner, and to a controlled depth, to define the pocket. The keratome is maintained in position relative to the eye by a suction ring 26 (FIG. 4) secured by vacuum suction about the cornea, and the keratome cuts into the cornea automatically relative to its attachment at suction ring 26. A micrometer arrangement (not shown) may be utilized to calibrate the trephine before insertion, thus to insure a predetermined cut depth.

The pocket or tunnel 23 thus defined, typically by automatic keratome, may typically be 4.0–11.0 mm long extending to within 1.5 mm of the opposing limbus. At least one-half of the circumference of the cornea remains intact throughout its layers, thus leaving the cornea well-supported, anteriorly by Bowman's membrane and posteriorly by Descemet's membrane. It may be noted that the cut by a keratome may be made without cutting of corneal tissue layers to a width equal to the cornea diameter.

The defined pocket may be of different shapes and sizes in accordance with the needs of respective patients, which may involve different degrees of ametropia, astigmatism, etc. An arcuate pocket is provided for astigmatism, and a relatively large pocket is provided for relatively large optical correction.

A spatula or glide to be inserted into the pocket is selected or determined, as to width, length, etc., according to the size and configuration of the pocket defined, which varies with the patient's refractive problem.

It may be noted that, in a modification of the procedure, the eye may be softened by using oral medication to stop inflow of fluid to the eye, thereby reducing pressure in the eye, thus to allow the spatula to be inserted without deforming the anterior or posterior walls of the pocket, thus to insure more accurate laser ablation of wall surfaces.

The spatula is thin and may typically be formed of plastic or metal, and preferably has a rounded end portion.

An important feature of the invention is that the spatula has on its anterior surface one or more reflective or mirror surfaces of selected configurations on its anterior surface, or has therein openings or open areas of selected configurations, thus to accommodate different types and degrees of patient optical problems to be corrected. These may include different degrees of far-sightedness, hyperopia and astigmatism.

Instead of being defined on a spatula, reflective areas or openings may be defined on and in the dissector, or the keratome cutting blade, for reflection of the laser beam onto the anterior wall of the pocket, the blunt dissector or cutting blade serving to reflect the laser beam onto the anterior pocket wall for ablation of corneal tissue.

The configuration and sizes of reflective areas or openings in or on a spatula or cutting blade are determined in accordance with the type and degree of correction required for a patient's problems, such as different degrees of far-sightedness, near-sightedness, or degrees of astigmatism.

The laser beam is a finely defined beam and the pattern defined thereby and tissue being ablated is provided by pre-setting instructions into the computerized laser equipment.

Embodiments of the configurations of reflecting areas of spatulas are shown in FIGS. 6–14 and 16. Embodiments of openings defined in spatulas are shown in FIGS. 17–23. A reflective ring configuration 40 (FIG. 9) may be provided for different degrees of hyperopia. For different degrees of astigmatism, paired, arcuate reflective segments 44 (FIG. 16) may be provided. For myopia (near-sightedness), a disk area 35 (FIG. 6), or 36 (FIG. 7), may be utilized. Openings may be utilized for ablating tissue on the posterior wall of the pocket. Examples 45 include the opening 38 (FIG. 17), opening 46 (FIG. 20), paired openings 48 (FIG. 21) or 50 (FIG. 23) may be used for appropriate corrections, the last mentioned openings configurations being for different degrees of astigmatism.

A tube or passage 32 (FIG. 6) and 34 (FIG. 11) may be utilized to provide for air or gas passage therethrough from a pressurized source (not shown) for the cooling of a spatula and areas being ablated, and for the removal or venting of debris or break-down products of ablation by gas emitted via openings 33 in the tube 32.

Figure 16:
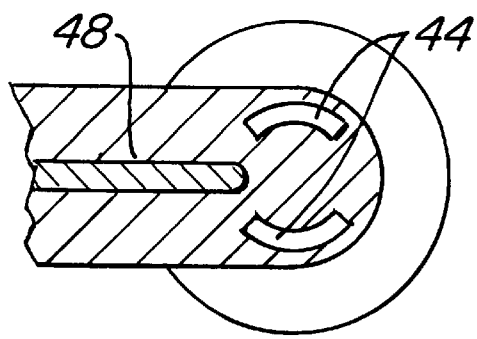
FIG. 16 is a plan view of the end portion of a spatula, showing reflective annular segments corresponding to the pocket portions of FIG. 15.
Figure 17:
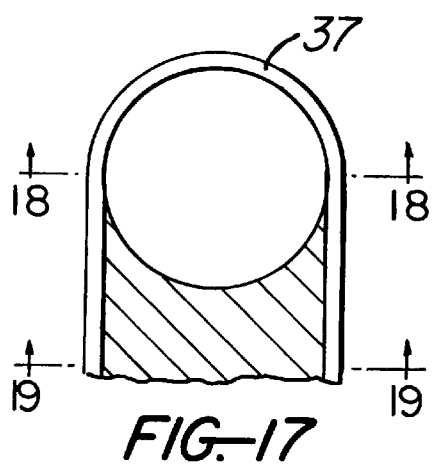
FIG. 17 is a plan view of a spatula end portion showing a large opening therein and a ridge thereabout.
Figure 18:
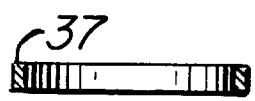
FIGS. 18 and 19 are sectional views taken, respectively, at lines 18—18 and 19—19 in FIG. 17.
Figure 20:
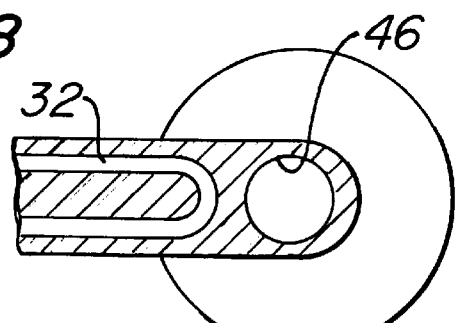
FIGS. 20–23 illustrate various configurations of openings defined in spatulas utilized with the invention for defining areas of corneal tissue to be ablated.
Figure 19:
Figure 21:
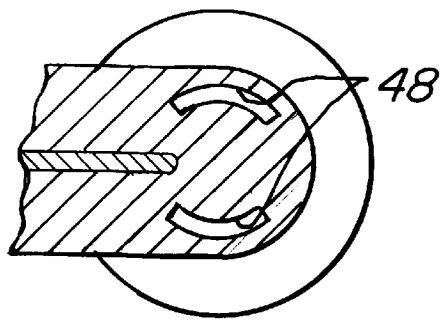
Figure 22:
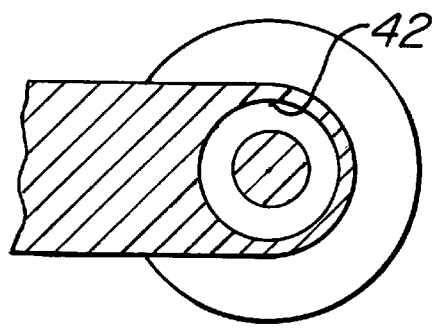
Figure 23:
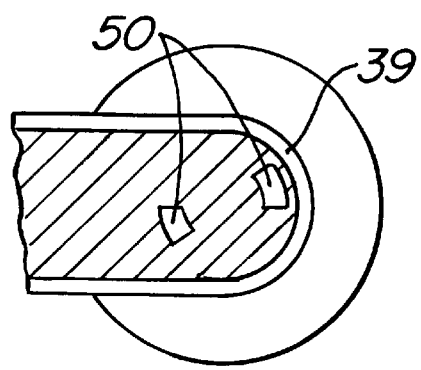

As indicated in FIG. 16, a suction or vacuum intake 48 may be provided, this intake being connected with a suction source (not shown) to withdraw gases and debris from the areas of ablation.

In a modification, a spatula may have a thickened, rounded lower portion (FIG. 12) which serves to insure a flat anterior surface of the spatula for the incidence thereon of a laser beam for accurate reflection therefrom.

A ridge, typically an anterior ridge, may be provided on a too spatula, as indicated at 37 (FIGS. 17–19), and 39 (FIG. 23), thus to provide a space for the venting of fumes or debris from areas of ablation, and to enable improved laser focusing.

In a modified form of mirror arrangement (not shown), the laser beam is reflected by a mirror disposed in a pocket in an inclined orientation. A pocket may be deepened or widened for this purpose by removing aqueous fluid from the anterior chamber of the eye, or by the use of oral medication or eyedrops to decrease the pressure in the eye. A viscoelastic material is then inserted into the pocket, whereupon the posterior wall of the pocket bulges into the anterior chamber of the eye, thus to provide space for such an inclined mirror (not shown) to be positioned to reflect a laser beam onto stroma tissue to effect ablation.

Figure 5:
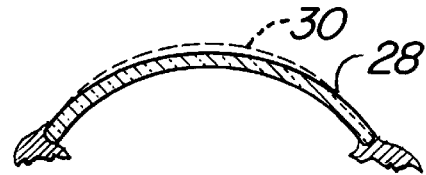
FIG. 5 is a sectional view of the anterior portion of an eye, showing the cornea before keratotomy in broken lines and showing in solid line the configuration after keratotomy.
Figure 6:
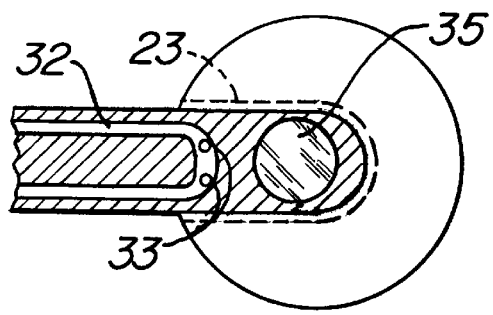
FIGS. 6 through 10A show different configurations of reflective areas on spatulae utilized according to the invention and used in laser ablation of corneal tissue.
Figure 7:
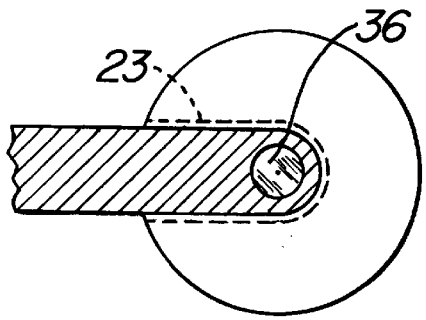
Figure 8:
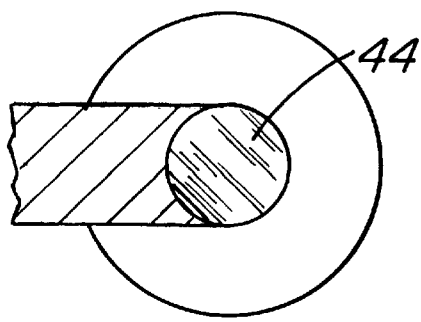
Figure 9:
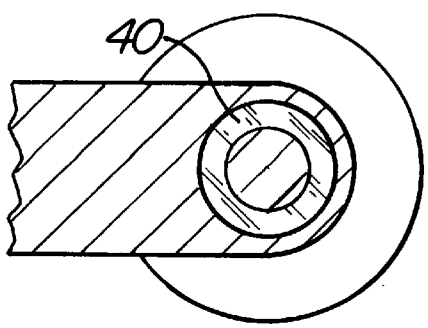
Figure 10:
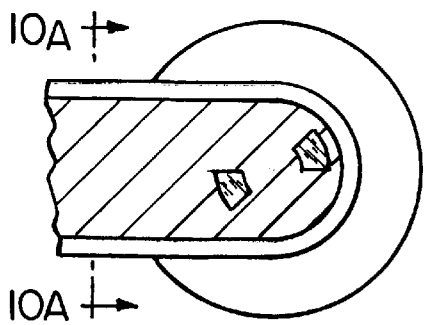
Figure 10A:
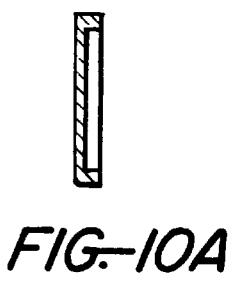
Figure 11:
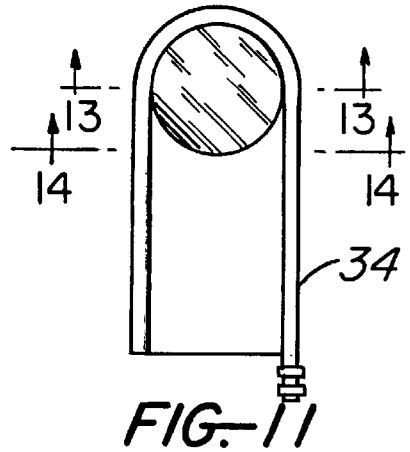
FIG. 11 is a plan view of a spatula having thereon a disk-shaped reflective area and a tubular element extending thereabout for cooling fluid or gas to vent any debris from laser ablation.
Figure 12:
FIG. 12 is a side view of the spatula of FIG. 11.
Figure 13:
FIGS. 13 and 14 are sectional views taken, respectively, at lines 13—13 and 14—14 in FIG. 11.
Figure 14:
Figure 15:
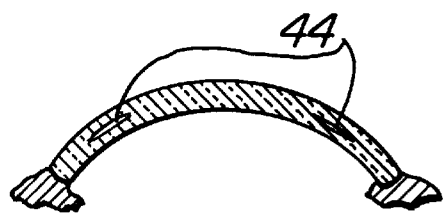
FIG. 15 is a sectional view of the anterior portion of an eye, showing annular segmental pocket portions defined in the cornea.

After laser ablation of the corneal stromal tissue, and the removal the spatula or blade from the corneal pocket, the anterior and posterior surfaces of the pocket are urged or compressed together by normal eye pressure, thereby changing the shape and the refractive power of the cornea and the eye. The original configuration is indicated at 30 in FIG. 5, and a relatively flatter configuration is indicated at 28. The radius of curvature of the altered cornea is greater than the radius of curvature before alteration.

Thus there has been shown and described apparatus and methods which fulfill all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. Apparatus for corneal keratotomy, comprising:
   an instrument for defining a pocket in a cornea generally transversely of the optical axis thereof,
   a laser device for directing a laser beam into the cornea in a direction generally toward the anterior surface of the cornea, and
   an insertion device sized and adapted for disposition in said pocket in the cornea,
   at least one defining feature on said insertion device to determine a configuration of at least one area to be ablated in a wall of said pocket by the laser beam, said at least one defining feature being one of
   (a) a reflective surface to reflect said laser beam on to the anterior wall of the pocket, or
   (b) an opening to pass the laser beam to the posterior wall of the pocket.

2. Apparatus in accordance with claim 1, wherein:
   said defining feature on the insertion device comprises at least one reflective surface configured to reflect said laser beam onto the anterior wall of the pocket to define a configuration of ablation of corneal tissue in accordance with the requirements of a patient.

3. Apparatus according to claim 1, wherein said reflective surface is of a generally disk configuration.

4. Apparatus according to claim 1, wherein the reflective surface is of annular configuration.

5. Apparatus according to claim 1, wherein said reflective surface comprises annular segments.

6. Apparatus according to claim 1, wherein the insertion device is a spatula having ridge means thereon to space apart anterior and posterior walls of the pocket.

7. Apparatus according to claim 6, wherein:

said ridge means is on the periphery of the spatula.

8. Apparatus according to claim 1, and further including passage means on said insertion device for conducting coolant fluid to cool ablated corneal tissue and the insertion device.

9. Apparatus according to claim 8, wherein said passage means has at least one opening for dispensing gaseous coolant fluid to remove debris resulting from laser ablation.

10. Apparatus according to claim 1, and further including suction means for drawing gases and debris from the area of tissue ablation.

11. Apparatus according to claim 1, wherein:

said defining feature comprises at least one opening for passage therethrough of the laser beam, said at least one opening being configured to define an area of corneal tissue to be ablated on said posterior wall of the pocket in accordance with the requirements of a patient.

12. Apparatus according to claim 11, wherein:

said insertion device defining features are on said instrument for defining the pocket in the cornea.

13. Apparatus according to claim 12, wherein said instrument for defining a pocket comprises a manual dissector.

14. Apparatus according to claim 12, wherein the instrument for defining a pocket comprises a keratome blade.

15. Apparatus according to claim 11, wherein said at least one opening is of a generally disk configuration.

16. Apparatus according to claim 11, wherein said at least one opening is of annular configuration.

17. Apparatus according to claim 11, wherein said at least one opening comprises annular segments.

18. Apparatus according to claim 1, wherein:

said insertion device defining features are on said instrument for defining the pocket in the cornea.

19. Apparatus according to claim 18, wherein said means for defining said pocket is a keratome blade.

20. Apparatus according to claim 18, wherein said means for defining said pocket is a manual dissector.

21. Apparatus in accordance with claim 1, wherein:

said insertion device has thereon said instrument for defining a pocket for separating corneal tissue to define said pocket, said insertion device having thereon at least one reflective surface configured according to the configuration of tissue to be ablated on the anterior wall of said pocket.

22. Apparatus according to claim 21, wherein said dissector is arcuate in configuration for separating lamellar corneal tissue to define an arcuate pocket.

23. Apparatus according to claim 1, wherein:

said instrument for defining a pocket comprises a sharp blade.

24. Apparatus according to claim 1, wherein:

said instrument for defining a pocket comprises a keratome having an oscillating blade.

25. Apparatus according to claim 1 wherein said defining feature is a reflective surface.

26. Apparatus according to claim 1 wherein the defining feature is an opening.

27. Apparatus according to claim 1 wherein a plurality of defining features comprise reflective surface areas.

28. Apparatus according to claim 1 wherein a plurality of defining features comprise openings in the insertion device.

29. A method of corneal laser keratotomy comprising the steps of:

defining a pocket in the cornea having anterior and posterior walls, inserting an insertion device into said pocket, said insertion device having at least one defining feature to determine at least one area of corneal tissue to be ablated in a wall of the pocket, said at least one defining feature being one of (a) a reflective surface to reflect said laser beam on to the anterior wall of the pocket, or (b) an opening to pass the laser beam to the posterior wall of the pocket, and applying a laser beam via said insertion device to ablate said at least one area of corneal tissue.

30. A method according to claim 29, and further comprising a first step of cutting a slit to predetermined depth in the anterior surface of the cornea for said pocket to extend therefrom.

31. A method according to claim 29, and further including removing the insertion device from the pocket to enable closure of the pocket by fluid pressure in the eye of the patient.

32. A method according to claim 29, wherein said at least one area is of a generally disk configuration.

33. A method according to claim 29, wherein said at least one area is of annular configuration.

34. A method according to claim 29, wherein said at least one surface comprises annular segments.

35. A method according to claim 29, wherein said insertion device comprises an opening therein of generally disk configuration.

36. A method according to claim 29, wherein said means defining at least one area comprises an opening of annular configuration.

37. A method according to claim 29, wherein said means for defining at least one area comprises annular segments.

38. A method according to claim 29, and further including removing gas and debris from the area of ablation.

39. A method according to claim 29, and further including cooling the ablation area of tissue and the device.

40. A method according to claim 29, wherein:

said pocket is defined by the insertion and manipulation of a dissector to separate corneal lamellar tissue.

41. A method according to claim 29, wherein said pocket is defined by operation of a keratome to accurately define said configuration of said pocket and the depth thereof.

42. A method according to claim 26, and further comprising the step of directing said laser beam in a general direction of the optical axis of the eye.

* * * * *